United States Patent [19]

Dickson

[11] Patent Number: 4,458,687
[45] Date of Patent: Jul. 10, 1984

[54] TRANS-TELEPHONIC ACOUSTICAL AND ELECTRICAL HEART VALVE MONITOR SYSTEM

[75] Inventor: Dale A. Dickson, Fridley, Minn.

[73] Assignee: Medtronic, Inc., Minneapolis, Minn.

[21] Appl. No.: 407,537

[22] Filed: Aug. 12, 1982

[51] Int. Cl.³ .............................................. A61B 5/04
[52] U.S. Cl. ..................................... 128/639; 128/715
[58] Field of Search ............................. 128/639–641, 128/644, 715, 904, 802, 803, 773

[56] References Cited

U.S. PATENT DOCUMENTS

| | | | |
|---|---|---|---|
| 3,602,216 | 8/1971 | Mae | 128/640 |
| 3,732,868 | 5/1973 | Willems et al. | 128/639 X |
| 3,788,317 | 1/1974 | McCormick | 128/641 |
| 3,942,517 | 3/1976 | Bowles | 128/641 |
| 3,946,744 | 3/1976 | Auerbach | 128/904 |
| 4,337,377 | 6/1982 | Van Riper et al. | 128/904 |
| 4,362,164 | 12/1982 | Little et al. | 128/639 |

FOREIGN PATENT DOCUMENTS 2644236 4/1978 Fed. Rep. of Germany ...... 128/639

Primary Examiner—Lee S. Cohen
Assistant Examiner—John C. Hanley
Attorney, Agent, or Firm—Reed A. Duthler; John L. Rooney; Joseph F. Breimayer

[57] ABSTRACT

A heart monitor for transtelephonic monitoring of heart activity and of the functioning of implantable heart valves. The monitor is provided with foam electrodes for monitoring heart activity and with a microphone for simultaneous acoustic monitoring of heart valve function. The monitor is adapted for easy use by the inclusion of an electrode gel reservoir and a pump for transferring gel to the electrodes. A cover for protection of the electrodes is provided. Movement of the cover to expose the electrodes activates the pump and moistens the electrodes with gel. Closing the cover seals the electrodes and prevents evaporation of the gel.

11 Claims, 6 Drawing Figures

TRANS-TELEPHONIC ACOUSTICAL AND ELECTRICAL HEART VALVE MONITOR SYSTEM

BACKGROUND OF THE INVENTION

1. Field of the Invention

This invention generally relates to portable heart monitors and particularly relates to transtelephonic heart monitors.

2. State of the Prior Art

Portable heart monitoring apparatus are well known to the art. Generally, such monitors analyze electrical activity of the heart as sensed by means of skin electrodes and generate an output signal in response thereto. The audio signal may be used either as a warning signal or to facilitate transmission of the derived information over telephone lines. Circuitry for accomplishing this function is disclosed in U.S. Pat. No. 3,742,483 issued to Stern and in U.S. Pat. No. 3,872,251 issued to Auerbach et al.

Acoustical monitoring of prosthetic heart valve function is relatively new to the art. Such a monitoring involves analyzing the acoustic characteristics of the functioning heart valve as sensed by means of a microphone placed upon the chest, over the heart, and generating an output signal in response thereto. Circuitry for accomplishing this function is disclosed in commonly assigned co-pending U.S. patent application Ser. No. 243,229, filed by Badzinski et al on Mar. 13, 1981 entitled "Monitoring System." At present, applicant knows of no such acoustical monitoring system suitable for in-home use by the patient.

Generally, portable heart monitors are provided with electrodes which are coupled to the monitors by means of cables, as illustrated in U.S. Pat. No. 3,991,747 issued to Stanly et al and in U.S. Pat. No. 3,934,507 issued to Sarnoff et al. This approach is inconvenient for the patient to use, and has a major drawback the problem of cable breakage, which can lead to inaccurate monitoring of cardiac function.

Recently, some portable heart monitors have incorporated electrodes attached directly to the monitor housing as in U.S. Pat. No. 3,547,107 issued to Chapman. These monitors have generally used metal electrodes, as in Chapman, which are subject to corrosion and oxidation which may act as insulative layers over the electrodes and interfere with their proper function over time. The "Cardiophone" monitor, illustrated on page 16 of *Medical Electronics*, June 1981, appears to use foam electrodes which, although immune to corrosion and oxidation, require regular moistening with electrode gel, a messy and time-consuming procedure. Application of an insufficient amount of gel can also interfere with proper functioning of the electrodes.

SUMMARY OF THE INVENTION

The present invention discloses a portable heart monitor which overcomes the disadvantages of prior art electrode structures and expands the usefulness of acoustical heart valve monitoring.

By providing, in a single monitor package, an acoustical heart valve monitor and an electrical heart monitor, analysis of the functioning of both the heart and the valve during the same time period is facilitated. This monitor system allows the monitoring physician to accurately correlate valve and heart functions to a degree unobtainable with sequential use of two independent systems, and therefore provides new and useful information. Proper functioning of the monitor requires simultaneous accurate placement of electrodes and microphone, which is accomplished by arranging the microphone intermediate three triangularly arranged electrodes. Because the electrodes and microphone are arranged in this fashion, locating the microphone directly over the heart allows the electrodes to flank the heart on three sides, maximizing the potential for detection of heart activity between at least two of the electrodes. An acoustical or magnetic transducer allows coupling of the device to a telephone. Acoustical insulation isolates the microphone from the transducer and prevents feedback which would interfere with the functioning of the device.

In addition, by providing a novel electrode system, the invention overcomes problems of prior portable heart monitor electrodes. By providing a reservoir for storing electrode gel and a pump for transferring gel from the reservoir to the electrodes, the messy and time-consuming procedure of moistening the conductive foam electrodes is eliminated. The invention employs a protective cover, which minimizes evaporation of gel and protects the foam electrodes against physical damage. The pump is coupled to the movement of the cover to expose the electrodes, resulting in a measured quantity of gel being applied to the electrodes with each use of the device. The patient therefore requires no special training or expertise to properly use the monitor. Further objects, features, and advantages of the invention will become apparent upon consideration of the following detailed description in conjunction with the drawings described below.

DETAILED DESCRIPTION OF THE PREFERRED EMBODIMENT

Figure 1:
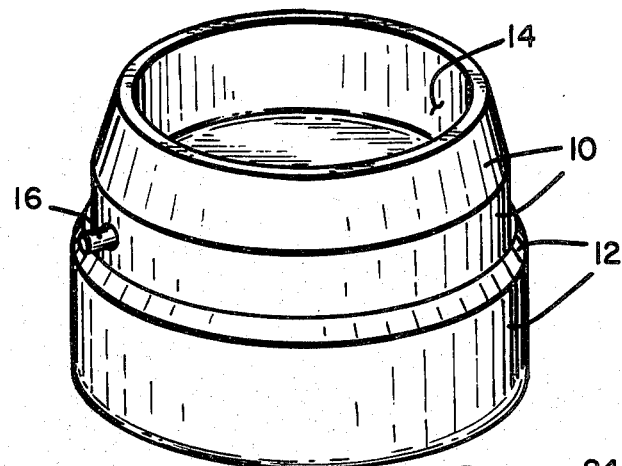
FIG. 1 shows a perspective drawing of a device according to the present invention.

FIG. 1 shows the complete device in perspective. The exterior of the device is comprised of a body 10 which is roughly cylindrical and has a recess 14 therein adapted to receive the mouth piece of a typical telephone. Protective cover 12 surrounds the bottom portion of body 10. Switch 16 extends from body 10 and is used to turn the device on.

Figure 2:
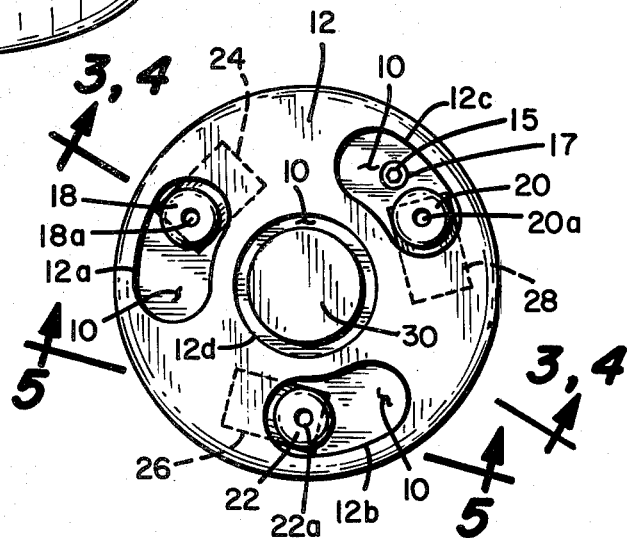
FIG. 2 shows a bottom plan view of a device according to the present invention.
Figure 3:
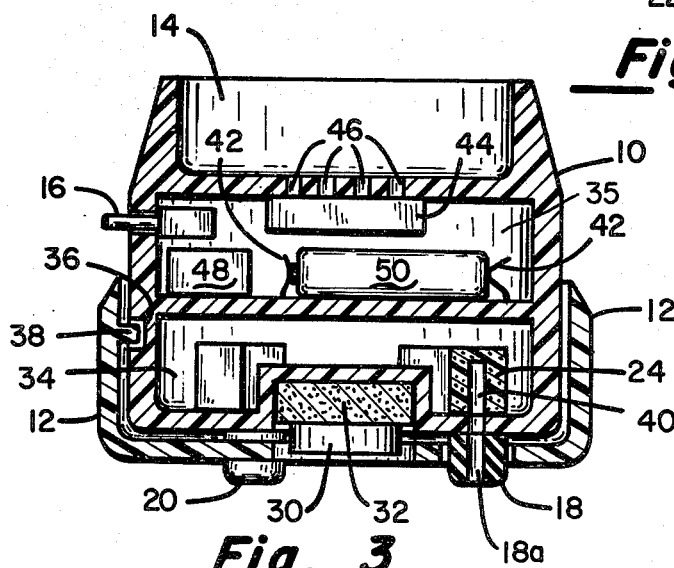
FIG. 3 shows a cross-sectional view of a device according to the present invention.

FIG. 2 shows a bottom plan view of the present invention. Cover 12 is seen to be provided with three elongated apertures 12a, 12b, and 12c. Foam electrodes 18, 20, and 22 are visible through aperatures 12a, 12b, and 12c respectively. Electrodes 18, 20, and 22 are provided with central bores 18a, 20a, and 22a respectively. Visible through elongated aperture 12a is threaded plug 15 which is screwed into threaded hole 17 which provides access to reservoir 34 (FIG. 3). Mounted within body 10 are three pumps which provide gel to the electrodes through their central bores. Pump bodies 24, 26, and 28 are illustrated by broken lines to show their location in relationship to electrodes 18, 20 and 22. Cover 12 is further provided with a fourth aperture 12d located centrally, which surrounds microphone 30, attached to body 10. This view shows the cover in an open position, with electrodes 18, 20 and 22 protruding through apertures 12a, 12b, and 12c.

FIG. 3 shows a cross-section of the device, along the plane indicated in FIG. 2. Within body 10 is reservoir 34 for storing a quantity of gel for moistening electrodes 18 and 20 and electrode 22 (not visible). Within reservoir 34 are pump bodies 24, 26 and 28. Pump body 24 is shown in cross-section, and is seen to be provided with a passage which connects to a central bore 18a of electrode 18. Cover 12 is shown in its open position, with electrodes 18 and 20 protruding therefrom. Cover 12 is moveable about body 10, its movement limited by interlocking pin 38 and groove 36. In its preferred embodiment, the device is provided with three such interlocking pins and grooves, however, for sake of simplicity, only pin 38 and groove 36 are shown. Mounted centrally within body 10 is microphone 30, which is mounted fixedly to sound insulation 32, which acoustically isolates microphone 30 from body 10. Above reservoir 34 is compartment 35 which contains the electrical components which may be incorporated in the device. For simplicity, these components are shown only as box outlines. The device is preferably powered by battery 50, held in place by battery clips 42. The output of the device is provided by transducer 44, which may be either a magnetic or acoustic transducer. Circuitry 48 receives information gathered from electrodes 18, 20, and 22 and microphone 30 and processes them for transmission through transducer 44. Switch 16 turns the device on. Circuitry 48 is interconnected with switch 16, transducer 44, battery 50, microphone 32 and electrodes 18, 20, and 22. For the sake of simplicity, these connections are not diagrammed, but are believed to be obvious to those skilled in the art. Apertures 46 allow the output of transducer 44 to proceed through to recess 14 and from there to an inserted telephone mouthpiece.

Figure 4:
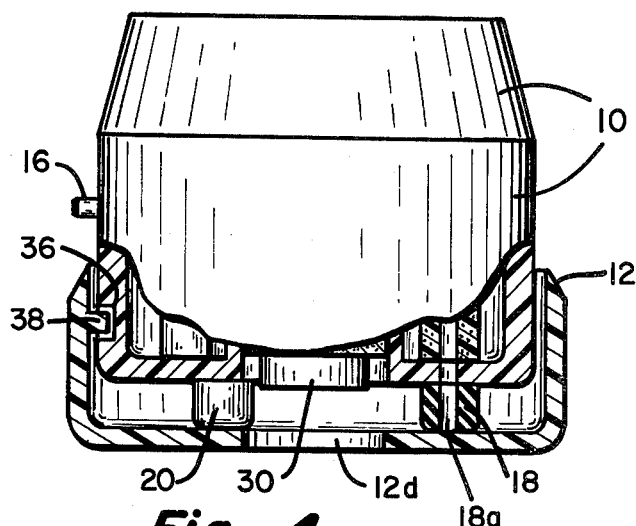
FIG. 4 is an incomplete cross-sectional view of a device according to the present invention, illustrating the operation of the cover.

FIG. 4 shows a cross-sectional view of the device with the cover in closed position. The cover is closed by rotating the cover approximately fifteen degrees in the clockwise direction as viewed from the top of the device, sliding the cover downward, and rotating the cover an additional forty-five degrees in the same direction. This displaces apertures 12a, 12b, and 12c from electrodes 18, 20, and 22. In the closed position, the inner surface of cover 12 is flush with the electrodes. Electrode 18 is shown in cross-section, illustrating that bore 18a is sealed by cover 12. Microphone 30 is now recessed behind cover 12, and thereby also provided with a degree of protection.

Figure 5:
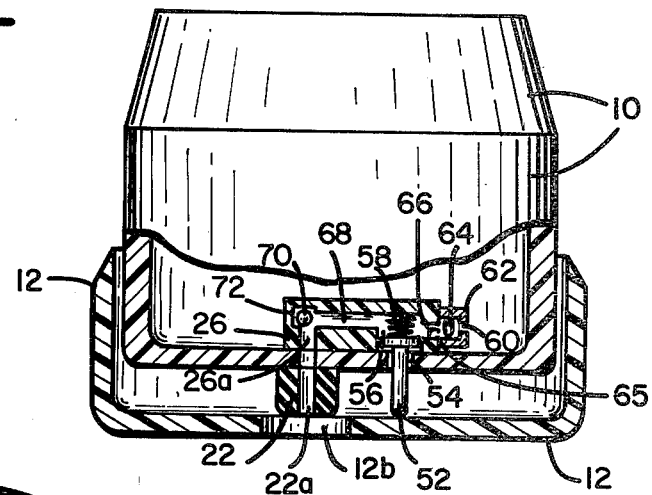
FIG. 5 is a further cross-sectional view of the device according to the present invention showing the construction of the pumps.

FIG. 5 shows a cross-section of the device, illustrating the pump mechanism. Located within reservoir 34 is pump body 26. Piston 52 protrudes from body 10 through aperture 54 and is mounted within cylinder 56 within pump body 26. Gel enters the pump mechanism through aperture 60 in check ball retainer 62. Check ball 64 prevents back flow out of aperture 60. Gel flows into cylinder 56 through aperture 65. Check ball 64 is prevented from sealing aperture 65 by means of guard 66. As piston 52 moves upward in cylinder 56, gel is forced through intermediate passageway 68 and out through pump passage 26a to central bore 22a of electrode 22. Backflow of gel into cylinder 56 is prevented by check ball 70 in check ball chamber 72. Thus, it can be seen that, when cover 12 is closed, piston 52 draws gel into cylinder 56. When cover 12 is opened, piston 52 forces gel out of cylinder 56 and through central bore 22a of electrode 22, moistening the electrode for use. The other two pumps of the device are identical in operation.

Figure 6:
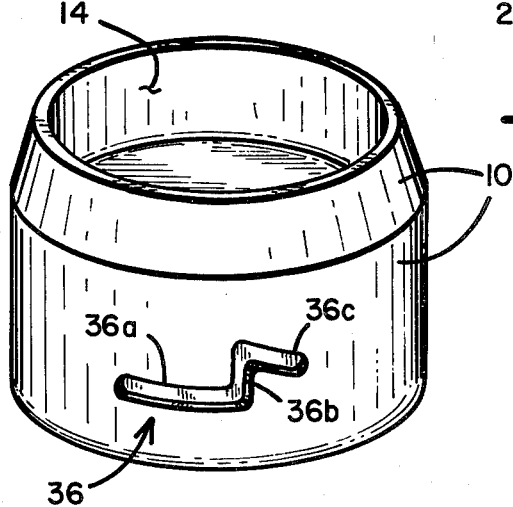
FIG. 6 is a perspective view of the body of the present invention showing details of the groove thereon.

FIG. 6 shows a perspective drawing of body 10, illustrating details of groove 36. Groove segments 36a is parallel to the bottom of body 10, and spans a distance of approximately forty-five degrees. Groove segment 36b allows for the vertical movement of the cover 10, during which gel is pumped into the electrodes. Segment 36c is provided with a slight downward slant relative to the bottom of body 10, and spans a distance of approximately fifteen degrees. The slight downward slant of groove segment 36c allows the springs within the pump mechanisms to hold the cover in open position.

Suitable materials for constructing the monitor system are well known to the art. Body 10, protective cover 12, pump bodies 24, 26 and 28, and piston 52 may be made of any rigid, impact-resistant plastic. Check balls 64 and 70, check ball retainer 62 and guard 66 are preferably stainless steel. Sound insulation 30 is preferably a closed cell foam, while electrodes 18, 20 and 22 are preferably open cell urethane foam.

PREFERRED MODE OF OPERATION

To operate the device, the patient places a telephone earpiece into recess 14, rotates cover 12 fourty-five degrees counter-clockwise, pushes cover 12 upward exposing the electrodes and providing them with gel, and rotates the cover a further fifteen counterclockwise degrees where it is stabilized by means of the pump springs. The device is then placed over the heart, with the electrodes in contact with the skin. Switch 16 is depressed to activate circuitry 48, microphone 30, and speaker 46. When the transmission is completed, the patient turns cover 12 fifteen degrees clockwise, the springs within the pumps push the cover down, filling the pump cylinders with gel for the next application, and the patient rotates the cover fourty-five degrees in a clockwise direction sealing the central bores of the electrodes, preventing evaporation of the gel. The device may then be stored until the next use. At periodic intervals, the patient or his physician may refill reservoir 34 with gel through threaded hole 17, preferably by means of hypodermic syringe.

While preferred forms and arrangements have been shown in illustrating the invention, it is to be clearly understood that various changes in detail and arrangement may be made without departing from the spirit and scope of this disclosure.

We claim:
1. A monitor system comprising:
   a monitor body having a first exterior surface;
   a reservoir within said monitor body for storage of electrode gel;
   at least two electrodes, mounted fixedly to the first surface of said monitor body and protruding therefrom, each of said electrodes having a central bore in fluid connection with said reservoir and open to the exterior of said electrodes;
   a cover movably attached to said monitor body having an inner surface facing the first surface of said monitor body and having an outer surface facing away from the first surface of said monitor body and having at least two apertures correspondingly arranged to said at least two electrodes such that said cover is locatable in a first position, a first distance from the first surface of said monitor body, at which said at least two electrodes protrude from said outer surface of said cover through said at least two apertures of said cover, said cover slideably moveable between said first position and a second position at which the apertures of said cover are displaced from said at least two electrodes and at which the inner surface of said cover is in contact with said at least two electrodes and seals the bores of said at least two electrodes.

2. A monitor system according to claim 1 further comprising pump means, mounted to said monitor body in fluid communication with said reservoir and with the bores of said at least two electrodes, for pumping gel from said reservoir to said at least two electrodes.

3. A monitor system according to claim 1 further comprising pump means mounted to said monitor body in fluid communication with said reservoir and with the bores of said at least two electrodes, for pumping said gel from said reservoir to said electrodes, coupled to said cover such that movement of said cover from said second position to said first position results in the pumping of gel from said reservoir to said at least two electrodes.

4. A monitor system according to claim 3 wherein said pump means is comprised of at least one pump which is comprised of a pump body having a pump bore substantially perpendicular to said first surface, a piston slideably mounted within the pump bore of said pump body and protruding slideably through an aperture in said first surface of said monitor body, and a spring mounted within the pump bore of said pump body urging said piston outward from the first surface of said monitor body and into contact with the inner surface of said cover.

5. A monitor system according to claim 4 wherein said at least one pump is further comprised of a first check valve means for allowing flow of gel from said reservoir into the pump bore of said pump body, but preventing flow of gel from the pump bore of said pump body into said reservoir whereby when said cover is moved from said first position to said second position, the pump bore of said pump body fills with gel.

6. A monitor system according to claim 5 wherein said pump is further comprised of a second check valve means for allowing flow of gel from the pump bore of said pump body to at least one of said electrodes but preventing flow of gel from said electrode to the pump bore of said pump body whereby when said cover is moved from said second position to said first position, gel is pumped from the pump bore of said pump body to at least one of said electrodes.

7. A monitor system according to claim 6 wherein said cover is further comprised of a first peg and wherein said monitor body has a first groove slideably receiving said first peg, said first peg and the groove of said monitor body determining the path of movement of said cover from said first position to said second position.

8. A monitor system according to claim 4, or claim 5, or claim 6, or claim 7 wherein said cover is slideably movable from said first position to a third position at which said cover is a second distance from the first surface of said monitor body greater than said first distance and said at least two electrodes protrude through the at least two apertures of said cover.

9. A monitor system according to claim 8 wherein said spring within the pump bore of said pump body, by means of said piston, is further adapted to stabilize said cover in said third position.

10. A monitor system according to claim 9 wherein the at least two apertures of said cover are elongated to permit movement of said cover from said first position to said third position while said at least two electrodes are protruding through the at least two apertures of said cover.

11. A monitor system comprising:
a monitor body having a first exterior surface;
a reservoir within said monitor body for storage of electrode gel;
at least one electrode, mounted fixedly to the first surface of said monitor body and protruding therefrom, having a central bore in fluid communication with said reservoir and open to the exterior of said at least one electrode;
a protective cover movably attached to said monitor body and moveable from a first position covering said bore of said at least one electrode to a second position exposing said at least one electrode; and
pump means for pumping gel to said at least one electrode, mounted to said monitor body, in fluid communication with said reservoir and with the bore of said at least one electrode, further coupled to said protective cover so that movement of said cover from said first position to said second position pumps gel from said reservoir to said at least one electrode.

* * * * *